United States Patent [19]

McConaghy, Jr.

[11] B 3,983,161

[45] Sept. 28, 1976

[54] OXIDATION OF UNSATURATED AMINES

[75] Inventor: John S. McConaghy, Jr., St. Louis, Mo.

[73] Assignee: Monsanto Company, St. Louis, Mo.

[22] Filed: Dec. 9, 1974

[21] Appl. No.: 530,925

[44] Published under the second Trial Voluntary Protest Program on February 24, 1976 as document No. B 530,925.

[52] U.S. Cl. .................. 260/465.9; 260/283 CN; 260/294.9; 260/464; 260/465 R
[51] Int. Cl.² ........................................ C07C 120/00
[58] Field of Search .......... 260/465 K, 465.9, 465 R

[56] References Cited
UNITED STATES PATENTS

| | | | |
|---|---|---|---|
| 2,375,015 | 5/1945 | Marple et al. | 260/465.9 |
| 2,375,016 | 5/1945 | Marple et al. | 260/465.9 |
| 2,471,927 | 5/1949 | Bortnick et al. | 260/465.9 |
| 2,849,478 | 8/1958 | Zubay et al. | 260/465.9 X |
| 3,719,701 | 3/1973 | Bach | 260/465.9 |

*Primary Examiner*—Joseph P. Brust
*Attorney, Agent, or Firm*—James C. Logomasini; P. L. Passley; N. E. Willis

[57] ABSTRACT

An oxidation process for the conversion of an unsaturated amine to an unsaturated nitrile in which the oxidation reaction takes place in the presence of a nitrogen base, a cuprous halide and an alcoholic compound.

12 Claims, No Drawings

OXIDATION OF UNSATURATED AMINES

BACKGROUND OF THE INVENTION

This invention relates to a process for the oxidation of unsaturated amines to unsaturated nitriles especially the oxidation of allylamine and methallylamine to acrylonitrile and methacrylonitrile respectively.

Polymers derived from unsaturated nitrile monomers such as acrylonitrile, methacrylonitrile, vinylidene cyanide, etc., are well known in the art. Of this class of monomers, acrylonitrile is presently the most important and is used in making a variety of commercial products e.g., butadiene-acrylonitrile copolymer rubbers, acrylonitrile-butadiene-styrene (ABS) copolymers and acrylic textile fibers.

Several means of producing acylonitrile have been proposed including dehydration of ethylene cyanohydrin, the direct reaction of acetylene and hydrogen cyanide and the catalytic amination of propylene followed by dehydrogenation of the proprionitrile so produced.

One of the more effective routes that is widely practised is the catalytic ammoxidation of propylene.

These processes, however, have the disadvantage of producing troublesome by-products and some, particularly the last mentioned, require the use of very expensive high pressure and high temperature equipment.

A further alternate process was disclosed in British Pat. Specification No. 570,835 granted to Shell Development Company on July 25, 1945. This process is one for the production of unsaturated nitriles from the corresponding unsaturated amine by reacting the amine with oxygen in the presence of a silver oxidation catalyst at a temperature of at least 450°C. The process is essentially a vapor phase reaction in which a mixture of the amine vapor, oxygen and an inert carrier gas are passed over a metal-alloy catalyst bed at about 500°C. This process has the disadvantage of requiring expensive and complex equipment and high temperatures.

A further development of the route from unsaturated amine to unsaturated nitrile is provided in U.S. Pat. No. 3,719,701 in which the amine is reacted with molecular oxygen in a solvent containing cuprous and cupric ions, the solvent being a nitrogen base. This process has many advantages in its simplicity, its relative freedom from undesirable by-products and its adaptability to continuous operation. It does, however, have the disadvantage that the yields obtained are quite low, the figure given for the conversion of allylamine to acrylonitrile using a cuprous chloride catalyst being 43.8%.

We have now discovered a modification of the above process by which the yield of nitrile from such a reaction can be substantially increased.

Accordingly it is an object of this invention to provide an improved process for the oxidation of an unsaturated amine to an unsaturated nitrile.

SUMMARY

The present invention provides a process for the oxidation of an unsaturated amine to an unsaturated nitrile which comprises reacting the amine with oxygen in the presence of a solution comprising a cuprous halide, a nitrogen base and an alcoholic compound having the formula R.OH wherein R is an alkyl, aryl, alkaryl or aralkyl radical, the reaction being carried out at a temperature of from 0° to 200°C.

The alcoholic compound can be an aliphatic alcohol such as methanol, ethanol, a butanol, a pentanol, an aryl alcohol such as phenol or naphthol, an aralkyl alcohol such as benzyl alcohol or an alkaryl alcohol such as cresol. Most frequently, however, it is aliphatic alcohol and preferably one having from 1 to 4 carbon atoms. The most convenient alcohol to use is ethanol.

The unsaturated amine used in the process of the invention is most conveniently one having the formula:

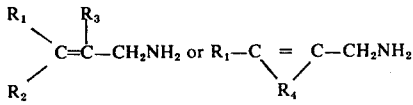

wherein $R_1$, $R_2$ and $R_3$ represent hydrogen or monovalent organic radical and $R_4$ represents a divalent organic radical, or, together with the two carbon atoms to which it is linked, an aromatic radical with the limitation that such radicals are not oxidizable and do not inactivate the catalyst under the reaction conditions used in the process.

Monovalent organic radicals of this description include alkyl, olefinically unsaturated aliphatic, cycloaliphatic, alkaryl, aromatic, heteroaromatic and halogenated hydrocarbon radicals, (e.g., chlorinated and brominated hydrocarbon radicals), and radicals of the formula:

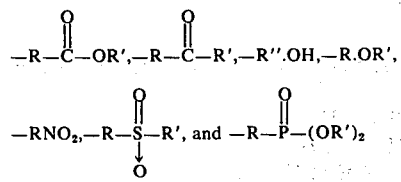

wherein R represents a divalent hydrocarbon radical, such as alkylene or phenylene, R' represents a monovalent hydrocarbon radical such as an alkyl or phenyl and R'' is alkylene or an olefinically unsaturated divalent radical. Representative monovalent radicals include:

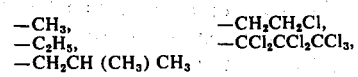

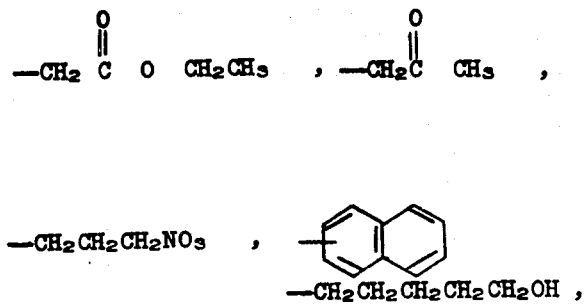

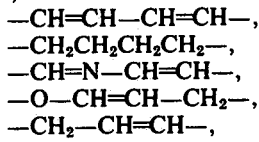

Divalent radicals of the foregoing description, i.e., R⁴, include:
—CH=CH—CH=CH—,
—CH₂CH₂CH₂CH₂—,
—CH=N—CH=CH—,
—O—CH=CH—CH₂—,
—CH₂—CH=CH—, and the like.

Generally, the unsaturated amines used in carrying out the process of the invention contain from 3 to 24 carbon atoms. Typical examples of such unsaturated amines and the corresponding unsaturated nitriles prepared therefrom by the process of the invention are:

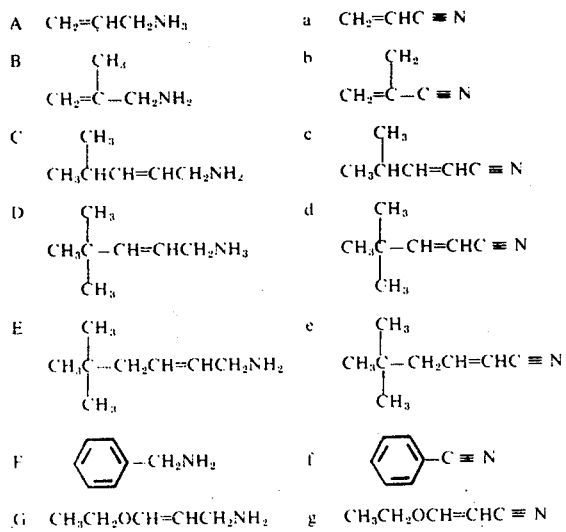

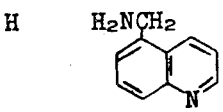 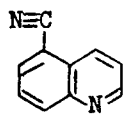

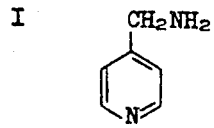 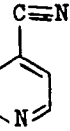

J HOCH₂CH₂CH=CHCH₂NH₂    j HOCH₂CH₂CH=CHC≡N

 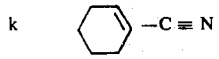

The amine reactant may consist of one amine or a mixture of amines. For example, benzonitrile and acrylonitrile may be prepared simultaneously by the process described herein by using, as the reactant, a mixture of benzylamine and allylamine.

The unsaturated amines useful in carrying out the process may be prepared by well known procedures described in the literature, e.g., by reacting the corresponding unsaturated halide, preferably the chloride or bromide with ammonia.

In carrying out the process defined herein the unsaturated amine reactant, as previously indicated, must not contain substituent groups which either are oxidizable or inactivate the catalyst under the process conditions. In this context oxidizable groups are primary or secondary amine groups, and ethynyl groups and groups which inactivate the catalyst are acid groups, such as carboxy and sulfo groups.

The catalyst comprises a mixture of a nitrogen base and a cuprous halide. The base and the cuprous halide form a complex and the activity of this catalytic complex is modified by the presence of the alcoholic compound.

The reaction mixture can often with advantage comprise a halide salt that is soluble in the nitrogen base. Among the halides the chloride and bromide are usually the most effective. This halide salt can be an alkali metal or alkaline earth metal halide and the most convenient metal component of the halide is lithium so that, where the halide is a metal salt it is usually lithium chloride or lithium bromide with the former being preferred. However, organic salts having a halide ion such as quarternary ammonium and phosphonium halides, e.g., tetra butyl ammonium chloride, tetra methyl phosphonium bromide and the like may be used.

The term "nitrogen base" is used herein to indicate an organic nitrogen compound containing a nitrogen compound having an unshared pair of electrons which can combine with a proton. All nitrogen bases which are not oxidized by cupric ions may be used and a list of such compounds can be readily prepared by a man skilled in the art. As specific examples of such compounds, the following are cited: hexamethylphosphoramide, N,N-dimethylacetamide, N,N-dimethylformamide, N,N-dimethylpropionamide, N,N-diethylacetamide, N-methylpyrrolidone, N-ethylpyrrolidone, triethylamine, tributylamine, diethylmethylamide, N-alkylpiperidines, quinolines, isoquinolines, N-alkylmorpholines, and pyridine. Of these bases pyridine is generally preferred. Mixtures of bases may also be used in the process of the invention.

In the usual practice of the invention, the nitrogen base functions also as the reaction medium, but this is not an essential feature of the process. In some cases, therefore, it might be preferred to use a reaction medium distinct from the nitrogen base. Suitable reaction media are those which are solvents for the nitrogen base and the cuprous halide and which do not interfere with the catalyst and are not oxidized to any appreciable extent thereby.

The proportions of the components of the mixture of cuprous halide and alcohol can vary widely but in general the molar ratio of cuprous chloride to alcohol can be from 10:1 to 1:100 and preferably from about 1:1 to 1:10. The amount of nitrogen base can also vary within wide limits so that the minimum possible (when the base does not form the reaction medium) is that necessary to complex the cuprous halide. When the base also provides the reaction medium, the amount used can of course be much greater.

The process can be operated at atmospheric or superatmospheric pressures and it is found that in many cases the use of pressures up to 500 psig confers substantial advantages. Within this range, pressures of 100 to 400 psig are preferred.

The temperature at which the reaction is conducted can be from 0° to 200°C. but in general temperatures of from 25° to 75°C. are satisfactory.

The catalyst can conveniently be prepared by adding the cuprous halide to the nitrogen base and the alcoholic compound (and optionally an inert solvent) with stirring then treating with oxygen until oxygen uptake ceases.

In a preferred mode of operation, molecular oxygen is used as the primary oxidant and may be introduced into the reaction medium by diffusion or injection techniques. Pure oxygen may be used, or alternatively, air or other gases containing free oxygen may be used as the oxidant. To obtain optimum yields of the desired nitrile products, a molar ratio of oxygen to amine of at least one is used and, preferably, a molar excess of oxygen to amine is used. However, higher or lower ratios may be used, if desired, since unreacted amine can be recovered and the yield of nitrile is substantially unaffected by using an excess of amine to oxygen.

When the batch process is used, the catalyst system may be prepared as indicated above, preferably at room temperature, and the unsaturated amine is added thereto under an atmosphere of oxygen with stirring for a period of time sufficient to ensure complete reaction. In this respect, a gas chromatograph has been found to be an excellent means for following the progress of the reaction. After completion, the nitrile product may be separated from the reaction mixture by distillation and the reaction repeated after reactivation of the catalyst by treatment with oxygen.

Alternatively the catalyst, prepared in the manner previously described, can be added to a chilled solution of the unsaturated amine in an appropriate reaction medium (e.g., the nitrogen base used to prepare the catalyst) and then oxygen added to the reaction medium until approximately the theoretical volume thereof has been consumed. This can be measured with great accuracy by using a closed system and a gas buret.

When the continuous process is used, it is preferable that the cuprous halide/nitrogen base complex be prepared (with or without an inert solvent) and the alcoholic compound and unsaturated amine be added thereto. In such a process the amine is conveniently added at a slow rate to the reaction mixture while simultaneously passing a stream of air, other oxidant gas mixture or molecular oxygen through the solution at a temperature and flow rate such that optimum reaction conditions are established with respect to nitrile product formation and the removal thereof from the reaction mixture by the gas sweep. The product is then removed from the exit gas stream by any well known method. The water formed as a result of the oxidation reaction may be removed from the nitrile by any suitable means such as by fractionation or the use of drying agents.

In actual operation, the optimum reaction conditions to be used in carrying out the process will depend on the reactants used, the oxidant selected, and whether the continuous or batch method is employed. The optimum conditions for a given specific reaction and method can be readily determined by a few preliminary experiments.

To further illustrate the invention, the following examples are given:

EXAMPLE I

This Example illustrates the effect of ethyl alcohol on the oxidation of allylamine using a cuprous chloride in pyridine catalyst.

A flask was equipped with a gas uptake measuring buret filled with oxygen. Cuprous chloride (0.50 gram) and pyridine (20 ml) were placed in the flask and this solution took up 31 ml of oxygen at room temperature. The temperature was raised to 50°C and 0.285 gram of allylamine were added. After two hours an acrylonitrile yield of 32% was obtained. Yield is defined as:

$$\frac{\text{Moles of Nitrile Produced}}{\text{Moles of Amine in Feed}} \times 100\%$$

In a parallel reaction under identical circumstances except for the addition of 0.58 ml of ethanol to the reaction mixture the yield obtained was 49%.

EXAMPLE 2

A further reaction identical to that performed in Example 1 except that the 0.50 gram of cuprous chloride was replaced by 0.145 gram of cuprous bromide gave yields of 44% in the absence of ethanol and 50% in the presence of 0.58 ml of ethanol.

The above Examples are for the purpose of illustration of the invention only and are not to be considered as limiting the scope thereof in any way.

It will be obvious to those skilled in the art that it is possible to devise modifications and variations of the invention herein disclosed. Accordingly, it is intended that all such modifications and variations which reasonably fall within the scope of the appended claims are included herein.

What is claimed is:

1. A process for the oxidation of an unsaturated amine having the formula

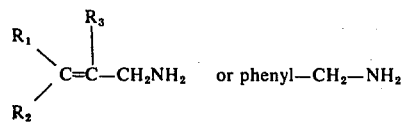

wherein $R_1$, $R_2$ and $R_3$ represent hydrogen or a $C_1$ to $C_4$ alkyl group, to the corresponding unsaturated nitrile which comprises reacting the amine with molecular oxygen in the presence of a solution in a nitrogen base which is not oxidized under the reaction conditions of;
 a. a cuprous halide and
 b. an alcoholic compound having the formula R—OH wherein R is an alkyl, aryl, alkaryl or aralkyl radical, in a halide to alcohol compound ratio of from 10:1 to 1:100, the reaction taking place at atmospheric or superatmospheric pressures and at a temperature of 0° to 200°C.

2. A process according to claim 1 in which the unsaturated amine is allylamine or methallylamine.

3. A process according to claim 1 in which the alcohol is an alkyl alcohol having from 1 to 4 carbon atoms.

4. A process according to claim 1 in which the cuprous halide is selected from cuprous chloride and cuprous bromide.

5. A process according to claim 1 in which the alcoholic compound is selected from the group consisting of methanol, ethanol, butanol, pentanol, phenol, naphthol, benzyl alcohol and cresol.

6. A process for the oxidation of an unsaturated amine selected from allylamine and methallylamine to acrylonitrile or methacrylonitrile respectively which comprises reacting the unsaturated amine with molecular oxygen at atmospheric or superatmospheric pressures and at a temperature of from 0° to 200°C in the presence of a solution in pyridine of a cuprous halide selected from cuprous chloride and cuprous bromide, and ethyl alcohol in a molar ratio of halide to alcohol of from 10:1 to 1:100.

7. A process according to claim 6 in which the reaction occurs at a pressure from 15 to 500 psig.

8. A process according to claim 6 in which a halide salt selected from lithium halides, tetra-alkyl phosphonium halides and tetra-alkyl ammonium halides is present in solution in the pyridine.

9. A process according to claim 8 in which a halide salt is lithium chloride and the molar proportion of lithium chloride to cuprous halide is from 3:2 to 5:2.

10. A process for the oxidation of an unsaturated amine selected from allylamine and methallylamine to acrylonitrile or methacrylonitrile respectively which comprises reacting the unsaturated amine with molecular oxygen in the presence of ethyl alcohol and a solution in pyridine of cuprous chloride and lithium bromide in a molar proportion of 1:2, the molar ratio of cuprous chloride to ethyl alcohol being from 10:1 to 1:100 and the reaction taking place at a temperature of from 0° to 200°C and a superatmospheric pressure of up to 200 psig.

11. A process according to claim 10 in which the unsaturated amine is allylamine and the unsaturated nitrile product is acrylonitrile.

12. A process according to claim 10 in which the unsaturated amine is methallylamine and the unsaturated nitrile product is methacrylonitrile.

* * * * *